(12) United States Patent
Koch et al.

(10) Patent No.: US 7,647,687 B2
(45) Date of Patent: Jan. 19, 2010

(54) METHOD OF MANUFACTURING A STENT

(75) Inventors: Steven J. Koch, Zimmerman, MN (US); Jeffrey A. Helgerson, Brooklyn Center, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 911 days.

(21) Appl. No.: 11/226,633

(22) Filed: Sep. 14, 2005

(65) Prior Publication Data

US 2007/0056151 A1    Mar. 15, 2007

(51) Int. Cl.
  *B23P 13/02* (2006.01)
  *A61F 2/82* (2006.01)

(52) U.S. Cl. .......................... 29/557; 29/558; 623/1.15; 623/1.16; 623/1.2

(58) Field of Classification Search .................... 29/557, 29/558; 623/1.15, 1.16, 1.2
See application file for complete search history.

(56) References Cited

U.S. PATENT DOCUMENTS

| | | | |
|---|---|---|---|
| 6,129,739 A | 10/2000 | Khosravi | |
| 6,299,755 B1 | 10/2001 | Richter | |
| 6,369,355 B1 | 4/2002 | Saunders | |
| 6,471,721 B1 * | 10/2002 | Dang | 623/1.34 |
| 6,572,647 B1 | 6/2003 | Supper et al. | |
| 6,660,021 B1 | 12/2003 | Palmer et al. | |
| 6,679,980 B1 | 1/2004 | Andreacchi | |
| 6,696,666 B2 | 2/2004 | Merdan et al. | |
| 6,776,022 B2 | 8/2004 | Kula et al. | |
| 6,805,898 B1 | 10/2004 | Wu et al. | |
| 2002/0017503 A1 | 2/2002 | Banas et al. | |
| 2002/0123795 A1 | 9/2002 | Jalisi | |
| 2003/0216803 A1 | 11/2003 | Ledergerber | |
| 2004/0000046 A1 | 1/2004 | Stinson | |
| 2004/0004061 A1 | 1/2004 | Merdan et al. | |
| 2005/0119723 A1 | 6/2005 | Peacock, III | |
| 2005/0228491 A1 | 10/2005 | Snyder et al. | |

FOREIGN PATENT DOCUMENTS

| | | |
|---|---|---|
| EP | 1 391 184 A1 | 2/2007 |
| WO | 01/87371 A2 | 11/2001 |

\* cited by examiner

*Primary Examiner*—Jermie E Cozart
(74) *Attorney, Agent, or Firm*—Crompton, Seager & Tufte LLC

(57) ABSTRACT

A stent, an intermediate article in the manufacture of a stent, and a method of forming a stent from a workpiece are disclosed. A portion of the wall thickness of a workpiece may be removed, demarcating the structural framework of a stent from the remainder of the workpiece material during a cutting process. In some embodiments, a residuum layer of material remaining after a cutting process may have a recessed surface in relation to a first surface of the structural framework of the stent formed in the workpiece. In some embodiments, a plurality of kerf channels may be cut in a workpiece to demarcate a structural framework of a stent from waste material of the workpiece. In some embodiments, a series of perforations may, at least in part, demarcate the structural framework of a stent from the remainder of the workpiece material. The waste material and/or residuum material may be removed from the structural framework of a stent during a post-cutting process.

13 Claims, 12 Drawing Sheets

METHOD OF MANUFACTURING A STENT

TECHNICAL FIELD

This invention generally relates to stents and methods of making a stent from a workpiece for placement within a body lumen or interior space of a body during a medical procedure.

BACKGROUND

Stents are expandable endoprosthetic devices adapted to be placed in a body lumen in order to maintain the patency of a body lumen by providing a flow pathway and/or structural support, for example. Stents are typically used in the treatment of atherosclerotic stenosis in blood vessels and the like to reinforce body vessels and to prevent restenosis following angioplasty in the vascular system. Additionally, stents may be used in the treatment of aneurysms, such as aortic aneurysms, by providing strength to a weakened vascular wall. They have also been implanted in other body lumens, such as urinary tracts and bile ducts. Stents are generally tubular structures that may be radially expandable between an unexpanded size and an expanded size greater than the unexpanded size. Therefore, a stent may be inserted through a body lumen in an unexpanded state and then expanded at a specific location within the lumen to an expanded state.

Stents, as well as other medical devices, are commonly intricately laser cut from a workpiece. The intricate nature of a stent is formed by removing large quantities of material from the workpiece, leaving a delicate structural framework of the stent. The structural framework may then be subjected to additional processes to generate a finished product. The intricate and delicate characteristics of the structural framework greatly reduce the dimensional and structural integrity of the stent, which may compromise subsequent manufacturing processes.

As the use of stents in a variety of medical procedures is gaining widespread acceptance, it is desirable to provide improved methods of manufacturing stents in order to increase efficiency, maintain structural integrity, and/or reduce dimensional inaccuracies. The disclosed stents and accompanying methods of manufacturing a stent may be deemed advantageous in view of the increased usage of stents during medical procedures.

SUMMARY

The invention is directed to stents for intraluminal placement and methods of manufacturing the same. An exemplary stent may be formed from a workpiece, such as a flat sheet or a tubular member.

Accordingly, one embodiment is an intermediate article in the manufacture of a stent, or stent perform, including a workpiece having a wall thickness. The workpiece may have a first surface and an opposing second surface. The first surface may include a raised surface defining a structural framework of a stent and a recessed surface defining a residuum layer of material of the workpiece. Thus, the structural framework may be distinguished from the residuum layer of material, yet the residuum layer of material may be connected to the structural framework. The residuum layer of material may provide structural and/or dimensional integrity to the structural framework of the stent during a manufacturing process. In some embodiments, the workpiece may include a plurality of kerf channels and/or perforations cut into the first surface of the workpiece.

A stent may be formed by providing a workpiece including a wall of material having a thickness defined between a first surface and a second surface. Material may be removed from the first surface of the workpiece such that only a portion of the wall thickness is removed, wherein the first surface of the workpiece has a raised portion defining a structural framework for a stent and a recessed portion defining a residuum layer of material remaining attached to the raised portion. In some embodiments, the workpiece may include a plurality of kerf channels and/or perforations cut into the first surface of the workpiece. The residuum layer of material may subsequently be removed from the structural framework of the stent during an additional manufacturing process.

BRIEF DESCRIPTION OF THE DRAWINGS

The invention may be more completely understood in consideration of the following detailed description of various embodiments in connection with the accompanying drawings, in which.

Figure 1:
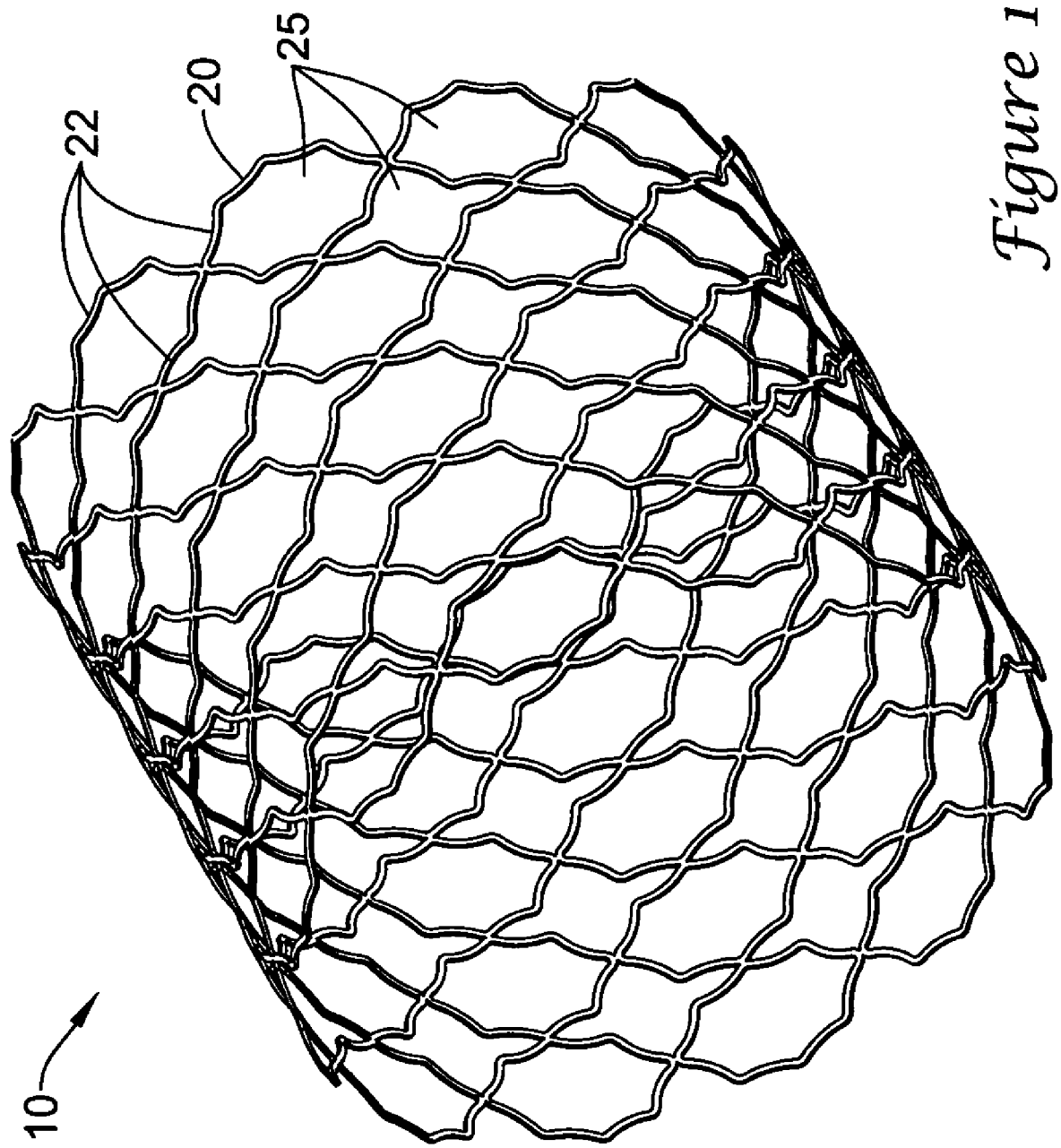
FIG. 1 is a perspective view of an exemplary stent in accordance with the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Referring now to the drawings, and particularly FIG. 1, illustrates an exemplary stent 10 within the scope of the invention. As discussed herein, the stent 10 may be formed from a workpiece. The workpiece may be a tubular member, a flat sheet, or the like. The stent 10 may be manufactured from a variety of materials. For example, the stent 10 may include a nickel-titanium alloy, such as a shape memory material commonly referred to as nitinol, which may provide the stent 10 with superelastic properties, psuedoeleastic properties, or linear elastic properties. Other suitable materials for the stent include, but are not limited to, stainless steels and their alloys, composites, platinum enhanced stainless steel, layered materials, niobium (Nb), zirconium (Zr), Nb—Zr alloys, tantalum (Ta), platinum (Pt), titanium (Ti), gold (Au), silver (Ag), magnesium (Mg), and alloys and compositions comprising the same. Polymers, polymer composites, and combinations and mixtures thereof, may also be used. The stent 10 may be treated or coated with an anti-thrombogenic agent, an anti-proliferative agent, an anti-inflammatory agent, or an anti-coagulant. Additionally or alternatively, the stent 10 may be treated or coated with a medication, such as a time-release drug. The stent 10 may also desirably have radiopaque characteristics for visualization on a fluoroscopy device, which may aid in proper placement of the stent 10 during a medical procedure. For example, the stent 10 may be doped with, plated with, or otherwise include a radiopaque material. Radiopaque materials are understood to be materials capable of producing a relatively bright image on a fluoroscopy screen or another imaging technique during a medical procedure. Some examples of radiopaque materials include, but are not limited to, gold (Au), platinum (Pt), palladium (Pd), tantalum (Ta), tungsten (W), plastic material loaded with radiopaque filler, and the like. The stent 10 may, alternatively or additionally, include MRI compatible materials and/or be coated with one or more MRI compatible coatings.

The stent 10 includes a structural framework 20 of a plurality of interconnected struts 22 defining a plurality of interstices or openings 25 located throughout the structural framework 20 between adjoining struts 22. The pattern of the structural framework 20 may be chosen to provide desired properties to the stent 10. For example, a chosen pattern may provide a desired amount of flexibility, expandability, and/or structural support.

Figure 2:
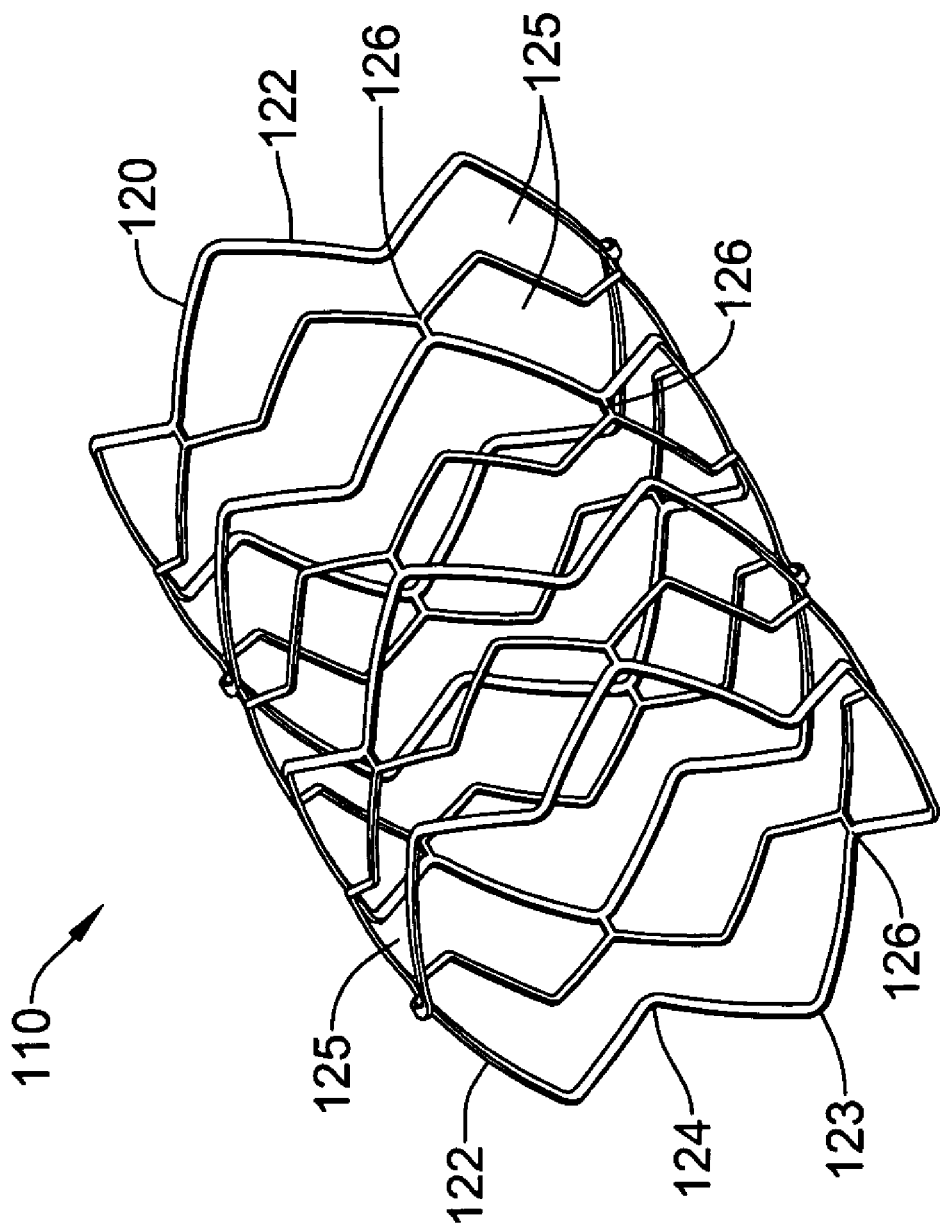
FIG. 2 is a perspective view of an alternative stent in accordance with the invention.

As shown in FIG. 2, an alternate embodiment of a stent 110 may include a structural framework 120 of a plurality of undulating filaments 122 having alternating peaks 123 and valleys 124. The plurality of undulating filaments 122 may be interconnected by a plurality of connectors 126 extending from one filament 122 to an adjacent filament 122. The connectors 126 may extend longitudinally between adjacent filaments 122 or otherwise extend between adjacent filaments 122. The connectors 126 may extend from a peak 123 of a first filament 122 to a valley 124 of an adjacent filament 122, from a peak 123 of a first filament 122 to another peak 123 of an adjacent filament 122, or from a valley 124 of a first filament 122 to another valley 124 of an adjacent filament 122, for example. However, the connectors 126 may extend from any portion of a first filament 122 to an adjacent filament 122. The filaments 122 and adjacent connectors 126 distinguish a plurality of interstices or openings 125 located throughout the structural framework 120 and bounded by adjacent filaments 122.

Figure 3:
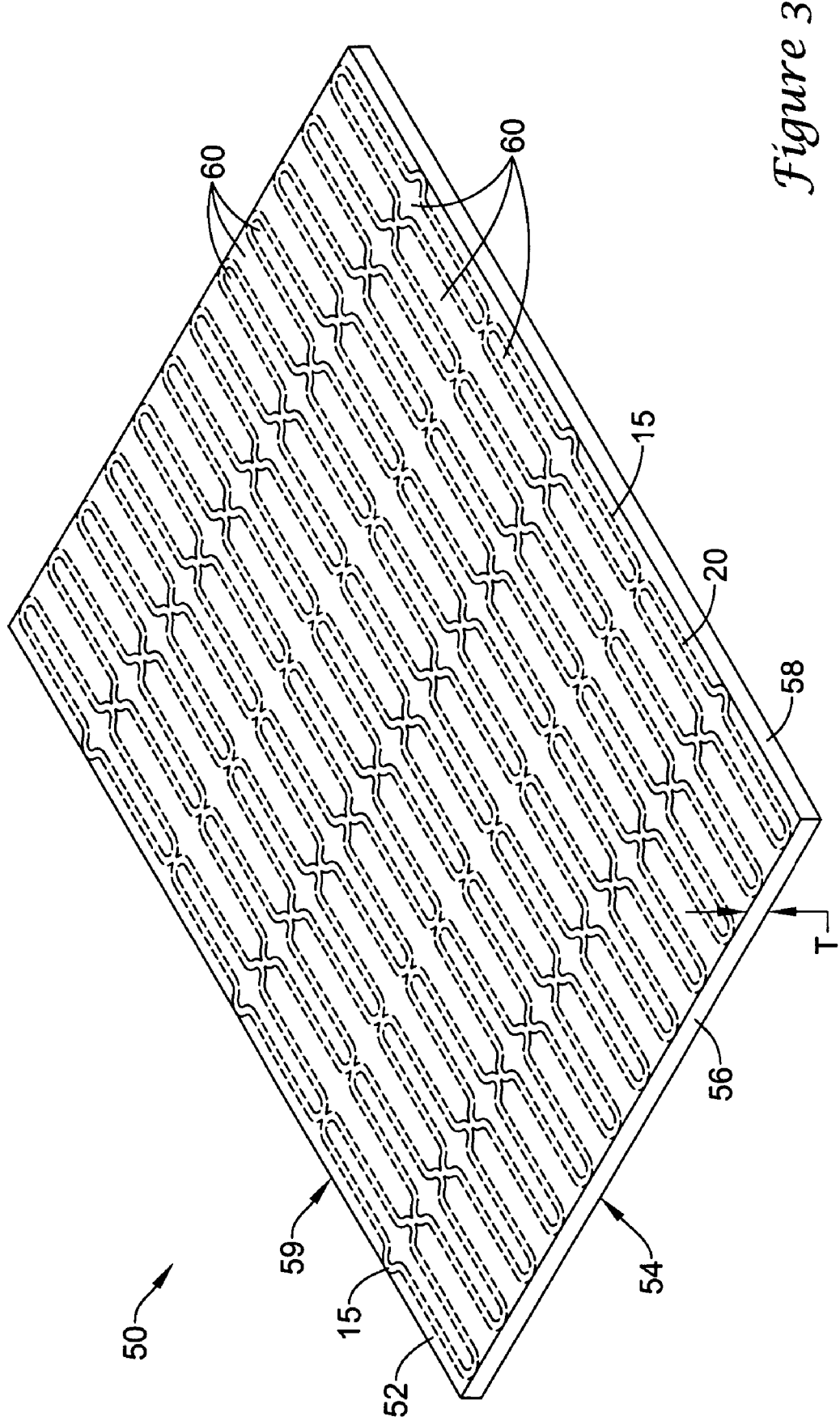
FIG. 3 is a perspective view of a workpiece for forming a stent, such as the exemplary stents illustrated in FIG. 1 or 2, in accordance with the invention.

A stent, such as the stent 10 illustrated in FIG. 1 or the stent 110 illustrated in FIG. 2, may be manufactured from a workpiece. The workpiece may be a flat sheet or a tubular member, for example. Referring to FIG. 3, a workpiece 50 may be a flat sheet of material having a first surface 52 and a second surface 54 opposite the first surface 52. The thickness T of material between the first surface 52 and the second surface 54 defines a wall 56. In some embodiments, the wall 56 may be of a uniform thickness, and in other embodiments the thickness of the wall 56 may vary throughout the length of the workpiece. For example, an intermediate portion of the workpiece 50 may be a different thickness, for instance thinner, than first and second end portions positioned on either side of the intermediate portion. The workpiece 50 may have a first edge 58 and a second edge 59 opposite the first edge 58. Each edge 58, 59 may extend between the first surface 52 and the second surface 54. Edges 58, 59 of the workpiece 50 may be brought together and secured to form a tubular member during a manufacturing process.

The phantom lines 15 shown in FIG. 3 illustrate an imaginary outline of the structural framework 20 of the stent 10 which may be manufactured from the workpiece 50. The phantom lines 15 are for illustrative purposes, and may not actually be visible on the surface 52 of the workpiece 50. The portion of the workpiece 50 located between the outline of the structural framework 20 for the stent 10 may be waste material 60 which may be removed from the structural framework 20 prior to providing the finished stent 10. The waste material 60 corresponds to the openings 25 of the stent 10 shown in FIG. 1, interposed between adjacent struts 22. Thus, the removal of the waste material 60 may provide the openings 25 interstitially located throughout the structural framework 20.

Figure 4:
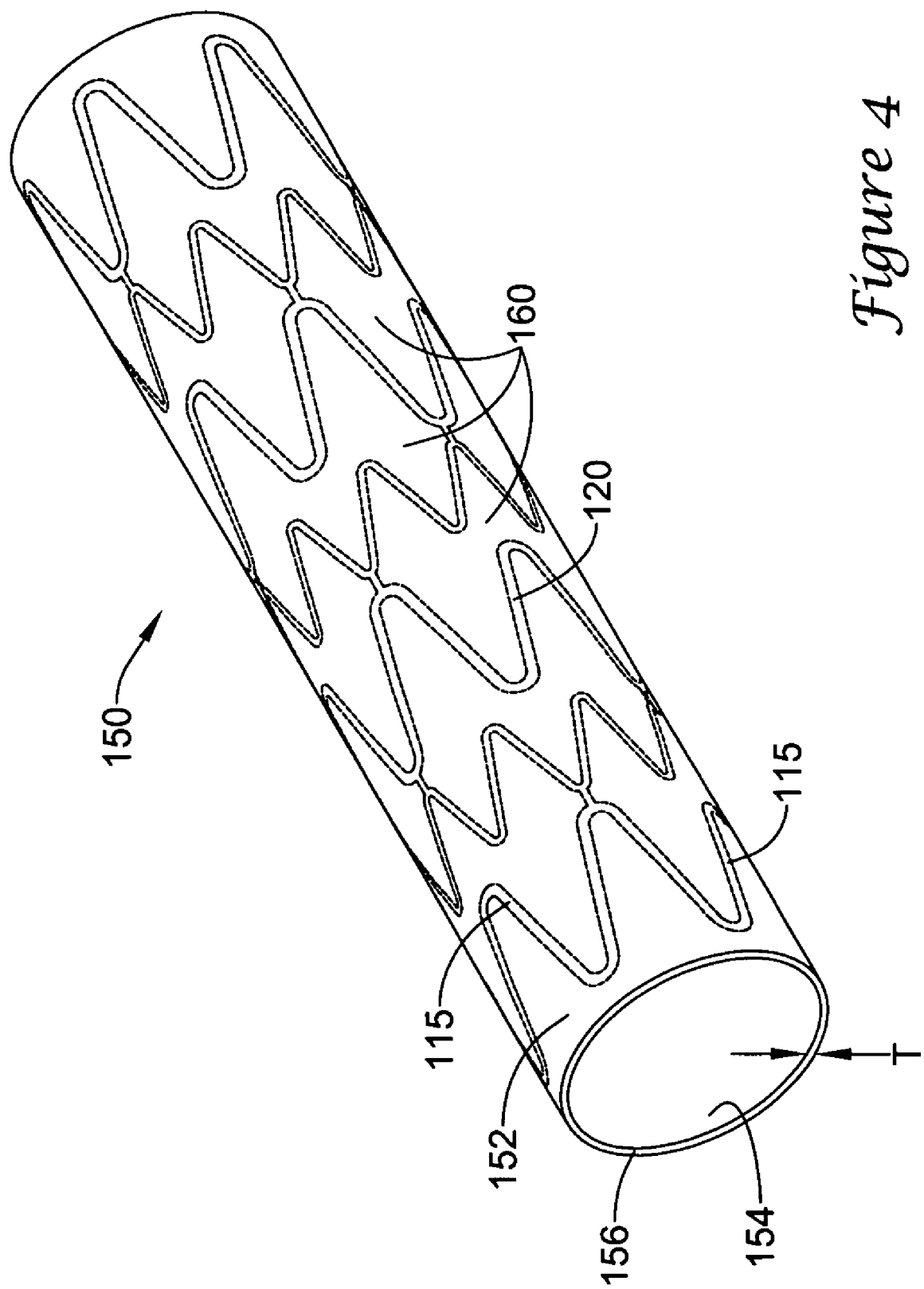
FIG. 4 is a perspective view of a workpiece for forming a stent, such as the exemplary stents illustrated in FIG. 1 or 2, in accordance with the invention.

Alternatively, a stent, such as the stent 10 illustrated in FIG. 1 or the stent 110 illustrated in FIG. 2, may be manufactured from a workpiece comprising a tubular member as shown in FIG. 4. The workpiece 150 may have a first, outer surface 152 and a second, inner surface 154 defining an annular wall 156 therebetween. The wall 156 may have a material thickness T between the first surface 152 and the second surface 154. In some embodiments, the wall 156 may be of a uniform thickness, and in other embodiments the thickness of the wall 156 may vary throughout the length of the workpiece. For example, an intermediate portion of the workpiece 150 may be a different thickness, such as thinner, than first and second end portions positioned on either side of the intermediate portion.

The phantom lines 115 shown in FIG. 4 illustrate an imaginary outline of the structural framework 120 of the stent 110 which may be manufactured from the workpiece 150. The phantom lines 115 are for illustrative purposes, and may not actually be visible on the surface 152 of the workpiece 150. The portions of the workpiece 150 interstitially located between the outline of the structural framework 120 for the stent 110 may be waste material 160 which will be removed from the structural framework 120 prior to providing the finished stent 110. The waste material 160 corresponds to the openings 125 of the stent 110 shown in FIG. 2, interposed between the filaments 122. Thus, removal of the waste material 160 may provide the openings 125 throughout the structural framework 120.

The structural framework of a stent, such as the stent 10 or the stent 110, may be formed from a workpiece. The pattern of the structural framework 20 may be cut into the workpiece 50 by a laser cutting device controlled by a computer automated system, for example a computer numerically controlled (CNC) machine. Such a laser cutting device may be able to replicate a very intricate and precise pattern of the stent 10. The laser may be a YAG laser, a $CO_2$ laser, an RF laser, a UV laser, an IR laser, a diode laser, etc., or any combination thereof. The laser may travel through a fluid jet, such as a water jet or other fluid medium. A laser beam, for example, or a laser beam traveling through a fluid jet may be directed at the workpiece 50. The workpiece 50 may be translated and/or rotated relative to the position of the laser, or vise versa, in order to cut the desired pattern of the structural framework 20. A fluid jet may be used to flush dross from the workpiece 50, provide cooling to the cutting zone, and/or ensure against physical or thermal defects to the workpiece 50 during the cutting process. Additionally, the cutting depth of a laser, such as a fluid-guided laser, may be precisely controlled. Thus, the laser may be controlled to remove only a portion of the wall thickness T of the workpiece 50. The speed and/or power of the laser may be selected to control the cutting depth of the laser. Each pass of the laser may remove a designated thickness of the workpiece 50. Additional passes could be used to reach a predetermined cut depth at select locations greater than the cut depth at other locations, and/or additional passes may be used to cut completely through the wall thickness T of the workpiece 50 at select locations while only cutting partially through the wall thickness T of the workpiece 50 at other locations. Alternatively or additionally, the speed and/or power of the laser may be increased/decreased during the laser cutting process to vary the cutting depth of the laser. One such laser cutting process is disclosed in U.S. Pat. No. 6,696,666 entitled Tubular Cutting Process and System, which is herein incorporated by reference in its entirety. Other cutting techniques may include optical etching, chemical etching, electron beam ablation, material deposition, as well as other laser ablation techniques.

Figure 5:
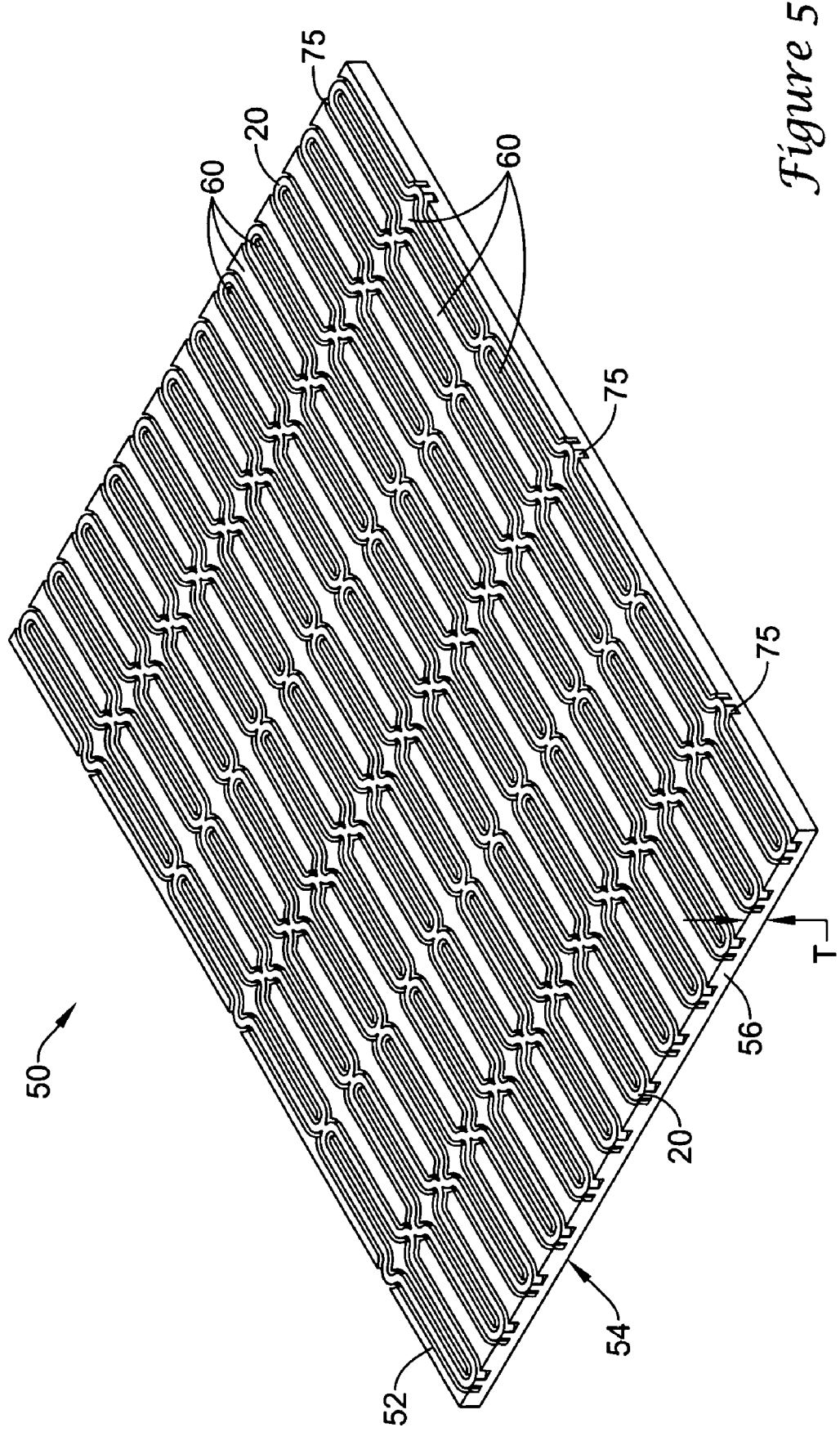
FIG. 5 is a perspective view of a workpiece in accordance with the invention having a plurality of kerf channels cut in one surface.

FIG. 5 illustrates the workpiece 50 including kerf channels 75 cut in the first surface 52 of the workpiece 50. The kerf channels 75 may outline the structural framework 20 of the stent 10 in the workpiece 50. A plurality of kerf channels 75 may form a plurality of closed pathways demarcating the structural framework 20 of the stent 10 from the waste material 60 of the workpiece 50. The kerf channels 75 may extend through only a portion of the thickness T of the wall 56 of the workpiece 50. The kerf channels 75 extending partially through the wall 56 of the workpiece 50 may have opposing edges, which, in some embodiments, may be parallel, and a bottom surface. Therefore, the second surface 54 of the workpiece 50 may remain substantially intact throughout the cutting process forming the kerf channels 75. In some embodiments, the second surface 54 may be uninterrupted by cuts or breaks during the cutting process of the kerf channels 75, thus preserving the structural and/or dimensional integrity of the workpiece 50. The kerf channels 75 may bound or otherwise define the extents of the waste material 60 of the workpiece 50.

The depth of the kerf channels 75 may be precisely controlled using a laser, such as a fluid-guided laser, as discussed above. For example, the speed and/or power of the laser may influence the depth of the kerf channels 75. Cutting limited depth kerf channels 75 distinguishes the structural framework 20 of the stent 10 from the waste material 60 of the workpiece 50, while maintaining the integrity of the workpiece 50 throughout the cutting process, as well as subsequent handling/processing of the stent 10. In some embodiments, by not cutting completely through the wall 56 of the workpiece 50, the workpiece 50 may be completely supported along the second surface 54 during the cutting process. In other words, the second surface 54 may be laid flat on a support surface such that the two surfaces contact and oppose one another. Therefore, the potential for the workpiece 50 to deflect or shift may be greatly diminished. Thus, cycle times may be shortened and/or toolpaths may be optimized due at least in part to the sustained structural and/or dimensional integrity of the workpiece 50. Additionally, since the kerf channel 75 does not extend to the second surface 54, dross will be prevented from accumulating on the second surface 54 during a cutting process.

Figure 6:
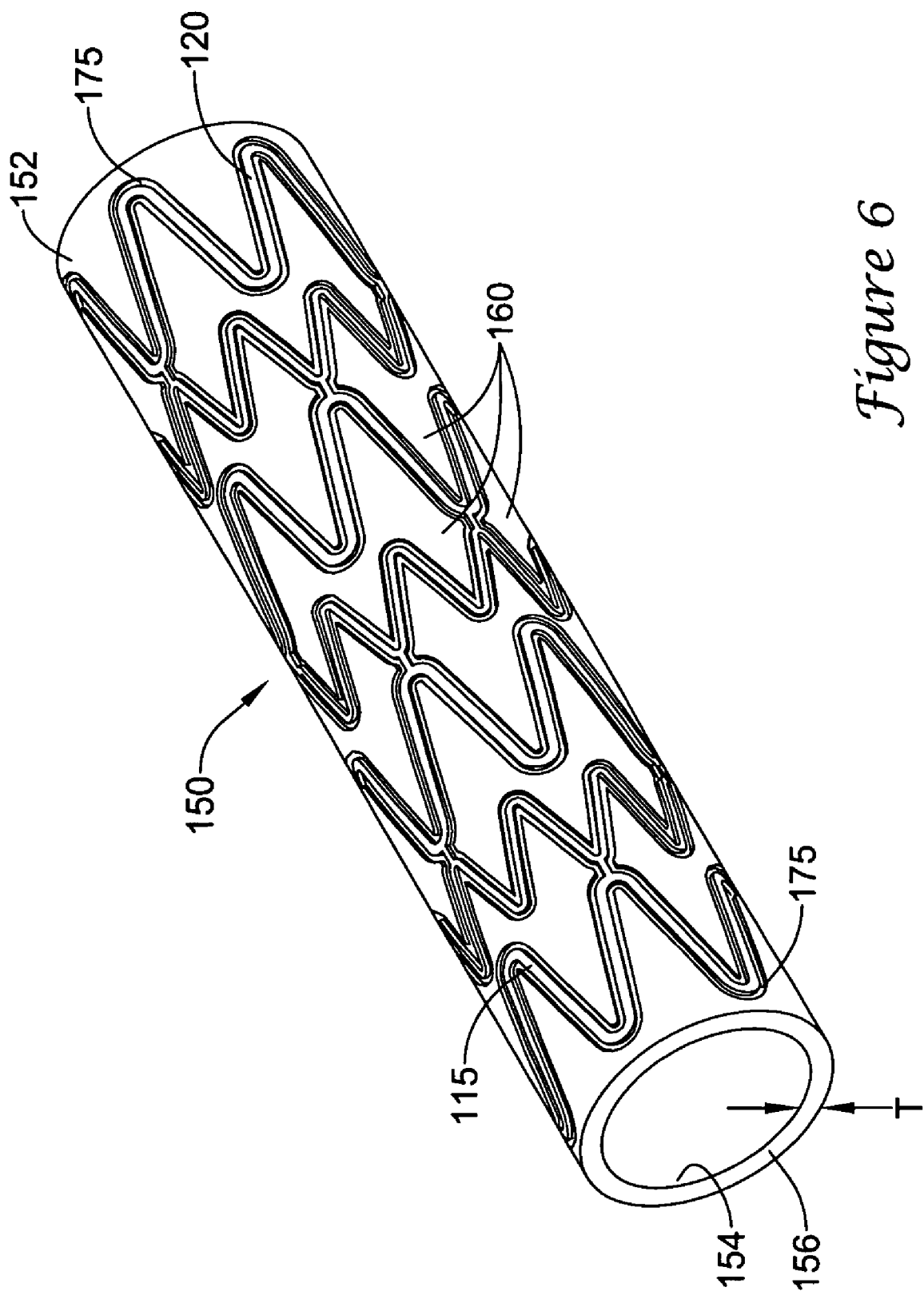
FIG. 6 is a perspective view of an alternative embodiment of a workpiece in accordance with the invention having a plurality of kerf channels cut in one surface.

FIG. 6 illustrates the workpiece 150 including a plurality of kerf channels 175 cut in the first, outer surface 152 of the workpiece 150. A plurality of kerf channels 175 may form a plurality of closed pathways demarcating the structural framework 120 of the stent 110 from waste material 160 of the workpiece 150. The kerf channels 175, similar to the kerf channels 75, may extend through only a portion of the thickness of the wall 156 of the workpiece 150. Thus, the kerf channels 175 extending partially through the wall 156 of the workpiece 150 may have opposing edges, which, in some embodiments, may be parallel, and a bottom surface. Therefore, the second surface 154 may remain substantially intact throughout the cutting process forming the kerf channels 175. In some embodiments, the second surface 154 may be uninterrupted by cuts or breaks during the cutting process of the kerf channels 175, thus preserving the structural and/or dimensional integrity of the workpiece 150. The depth of the kerf channels 175 may be precisely controlled using a laser, such as a fluid-guided laser, as discussed above. For example, the speed and/or power of the laser may influence the depth of the kerf channels 175. Cutting limited depth kerf channels 175 distinguishes the structural framework 120 of the stent 110 from the waste material 160 of the workpiece 150, while maintaining the integrity of the workpiece 150 throughout the cutting process, as well as subsequent handling/processing of the stent 110. The kerf channels 175 may bound or otherwise define the extents of the waste material 160 of the workpiece 150.

Figure 7:
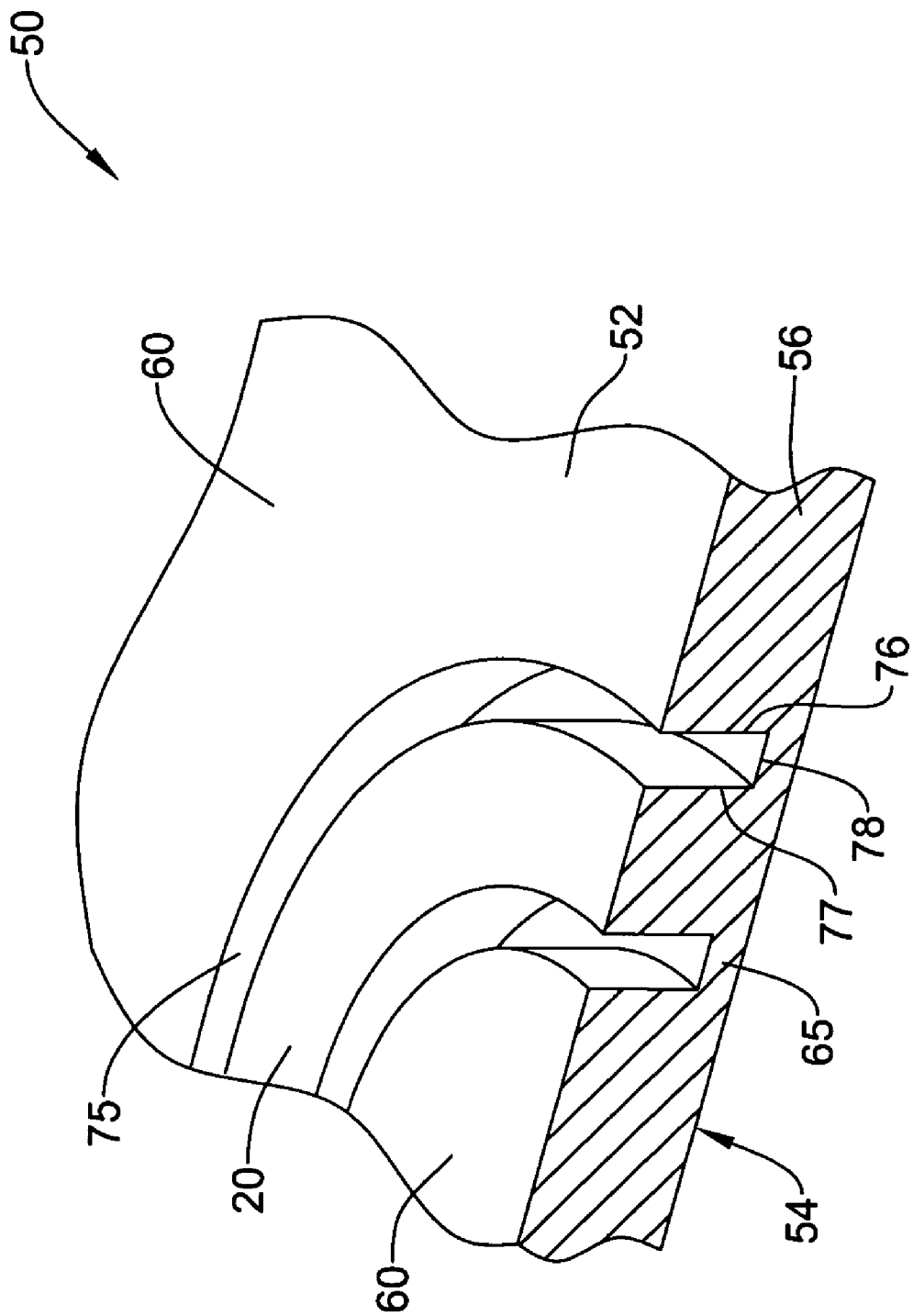
FIG. 7 is an enlarged perspective view of the workpiece illustrated in FIG. 5.

FIG. 7 is an enlarged view of the kerf channels 75 cut in the workpiece 50. It is noted that although FIG. 7 illustrates a flat workpiece as shown in FIG. 5, the discussion that follows is likewise relevant to kerf channels cut in a tubular workpiece such as shown in FIG. 6. The kerf channels 75 may generally follow the phantom lines 15 as shown in FIG. 3 to form an outline of the structural framework 20 of a stent. The kerf channels 75 may have a first edge 76, an opposing second edge 77, and a bottom surface 78. The kerf channels 75 differentiate the structural framework 20 of the stent 10 from the waste material 60, without completely separating the waste material 60 from the structural framework 20. A residuum layer of material 65 may be located between the bottom surface 78 of the kerf channel 75 and the second surface 54 of the workpiece 50. The residuum layer of material 65 has a reduced thickness less than the thickness of the workpiece 50. The residuum material 65 maintains a connection between the structural framework 20 and the waste material 60. This waste material 60 may not be completely removed from the structural framework 20 during the cutting process, but may be removed during a subsequent process. The residuum material 65 is uncut workpiece material remaining after the cutting process forming the kerf channels 75. The residuum layer of material 65 may be integrally connected with the waste material 60 and the structural framework 20. Thus, the residuum layer 65 connects or bridges the waste material 60 to the framework 20. The residuum material 65 provides support to the workpiece 50 throughout the duration of the cutting process, as well as after the cutting process is completed. Thus, the structural and/or dimensional integrity of the structural framework 20 may be retained.

Figure 8:
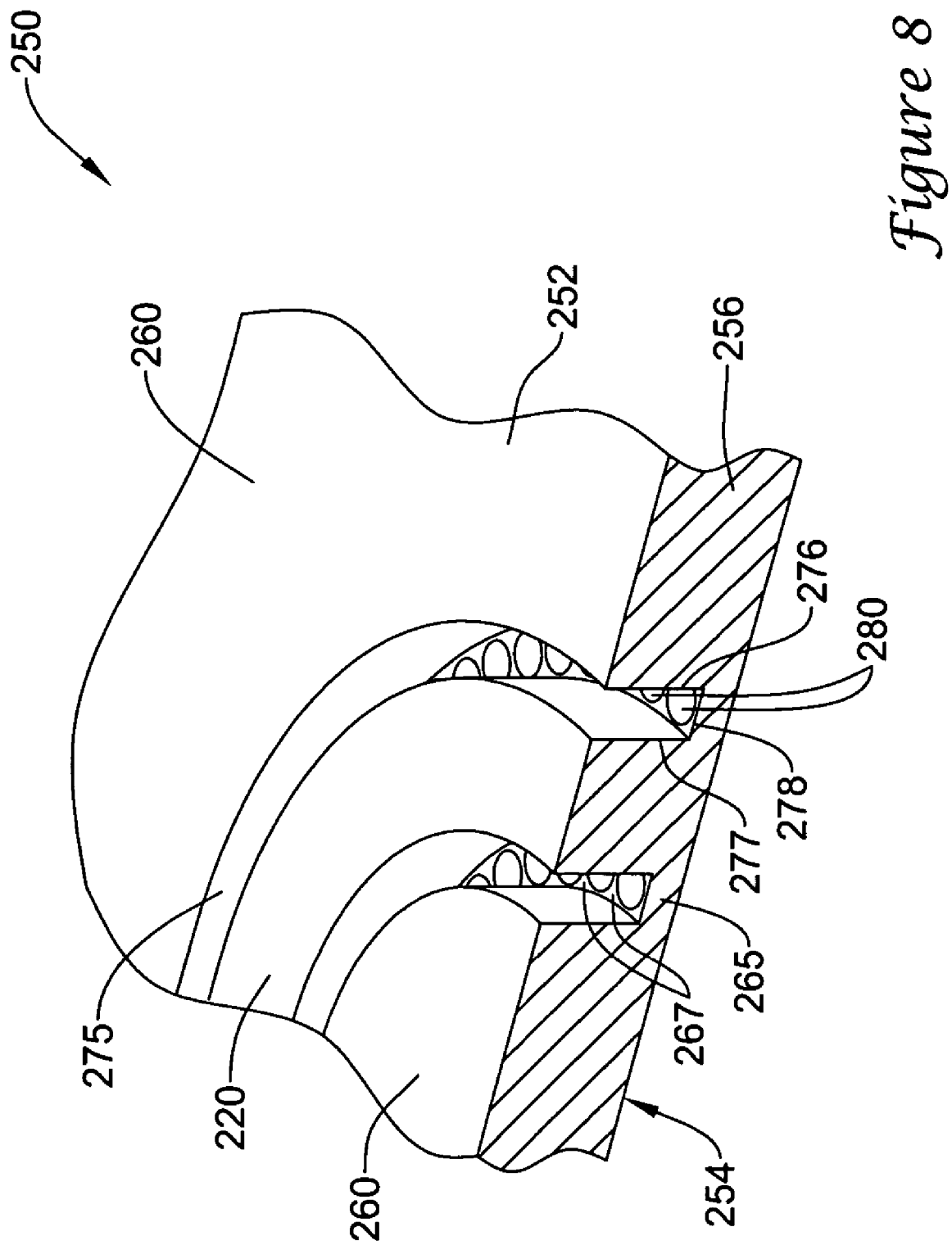
FIG. 8 is an enlarged perspective view of an alternative workpiece having a series of perforations cut through the wall of the workpiece.

FIG. 8 is an enlarged view of an alternate embodiment which may employ kerf channels. A plurality of kerf channels 275 may be similarly formed in a workpiece 250 as discussed above. The kerf channels 275 may have a first side 276, an opposing second side 277, and a bottom surface 278. In addition to cutting kerf channels 275 into the workpiece 250, a series of perforations 280 may be cut into the workpiece 250. As shown in FIG. 8, a series of perforations 280 may be cut through the residuum layer of material 265 between the bottom surface 278 of the kerf channel 275 and the second surface 254 of the workpiece 250. The perforations 280 may be apertures such as holes, gaps, or slots cut through the residuum layer of material 265. Additionally, the perforations may be circular, oval, square, rectangular, or any other shape. The perforations 280 may be uniformly spaced along a length of the kerf channel 275, or the perforations 280 may be more closely spaced in select locations relative to spacing of the perforations 280 throughout another length of the kerf channel 275. In some embodiments, the perforations 280 may be coextensive with the kerf channels 275. Although the series of perforations 280 illustrated in FIG. 8 are cut through the workpiece 250 in addition to the kerf channels 275, in some embodiments a series of perforations 280 may be cut into the workpiece 250 instead of the kerf channels 275. Thus, in some embodiments the perforations 280 may extend from the first surface 252 of the workpiece 250 to the second surface 254 of the workpiece 250 and may distinguish the structural framework 220 from the waste material 260. The series of perforations 280 may generally follow the phantom lines 15 shown in FIG. 3 in order to outline the structural framework 220 of the stent 210 in the workpiece 250. For example, a series of perforations 280 may bound or otherwise define the extents of a piece of waste material 260 corresponding to an interstitial opening of a stent. The series of perforations 280 may extend through the wall 256 of the workpiece 250, or the series of perforations 280 may extend only partially through the wall 256 of the workpiece 250. The perforations 280 remove a portion of the material of the wall 256 of the workpiece 250, yet the waste material 260 may remain connected to the structural framework 220 of the stent 210. As shown in FIG. 8, the waste material 260 may remain connected to the structural framework 220 by a bridging material 267 located between neighboring perforations 280. The bridging material 267 may be integral with the structural framework 220 and the waste material 260. By maintaining a connection between the waste material 260 and the structural framework 220 of the stent 210, the structural and/or dimensional integrity of the stent 210 may be maintained. The bridging material 267 may be removed from the workpiece 250 during a subsequent manufacturing process, thus separating the waste material 260 from the structural framework 220 of the stent 210.

Figure 9:
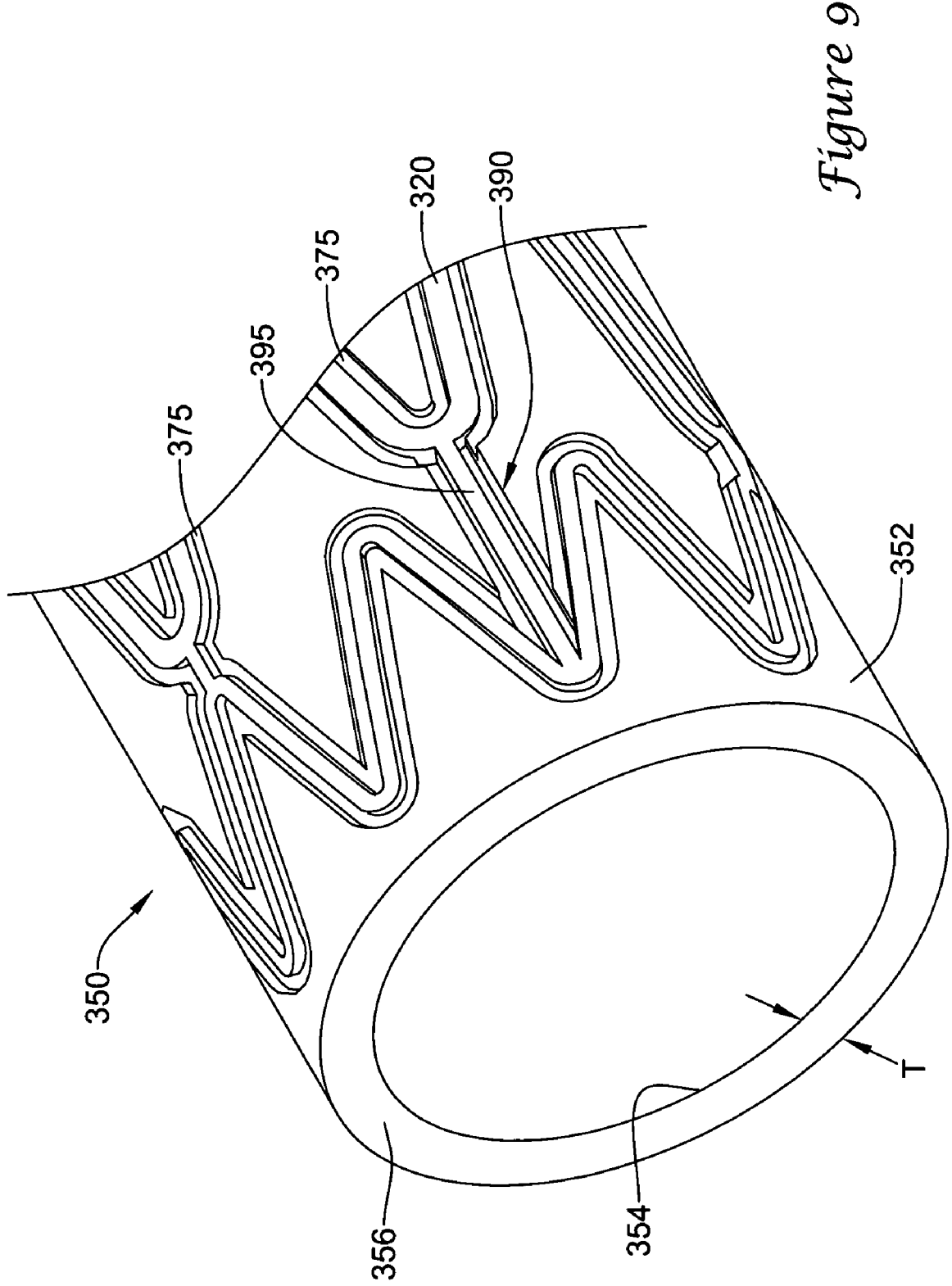
FIG. 9 is an enlarged perspective view of an alternative workpiece having a plurality of kerf channels cut in one surface and selective portions having cuts extending through the wall of the workpiece.

FIG. 9 is an enlarged view of an alternate embodiment employing kerf channels. A plurality of kerf channels 375 may be similarly formed in a workpiece 350 as discussed above. In addition to cutting the kerf channels 375 into the workpiece 350, material may be completely removed from the workpiece 350 at select locations. For instance, the cuts 390 may extend completely through the wall 356 to the second side 354 of the workpiece 350. Through cuts 390 may be formed in the workpiece 350 at select locations. In some embodiments, the cuts 390 may be formed on either side of a link 395. The link 395 may be a piece of material of the workpiece 350 extending between adjacent segments of the structural framework 320 of the stent 310. In some embodiments, a plurality of links 395 may extend between adjacent portions of the stent 310 throughout the structural framework 320. The link 395 may provide structural and/or dimensional integrity to the structural framework 320. In some embodiments, the link 395, or a portion thereof, may be removed during a subsequent manufacturing process. For example, the link 395 may be removed during a chemical-etching or electro-polishing process, or the link 395 may be mechanically cut or laser ablated, in order to remove the link 395 from the structural framework 320. The link 395 may have one or more frangible regions, such as regions of reduced cross-sectional area or including score lines, in order to remove the link 395 from the structural framework 320. Additional methods known in the art may be used to separate the link 395 from the structural framework 320.

Figure 10:
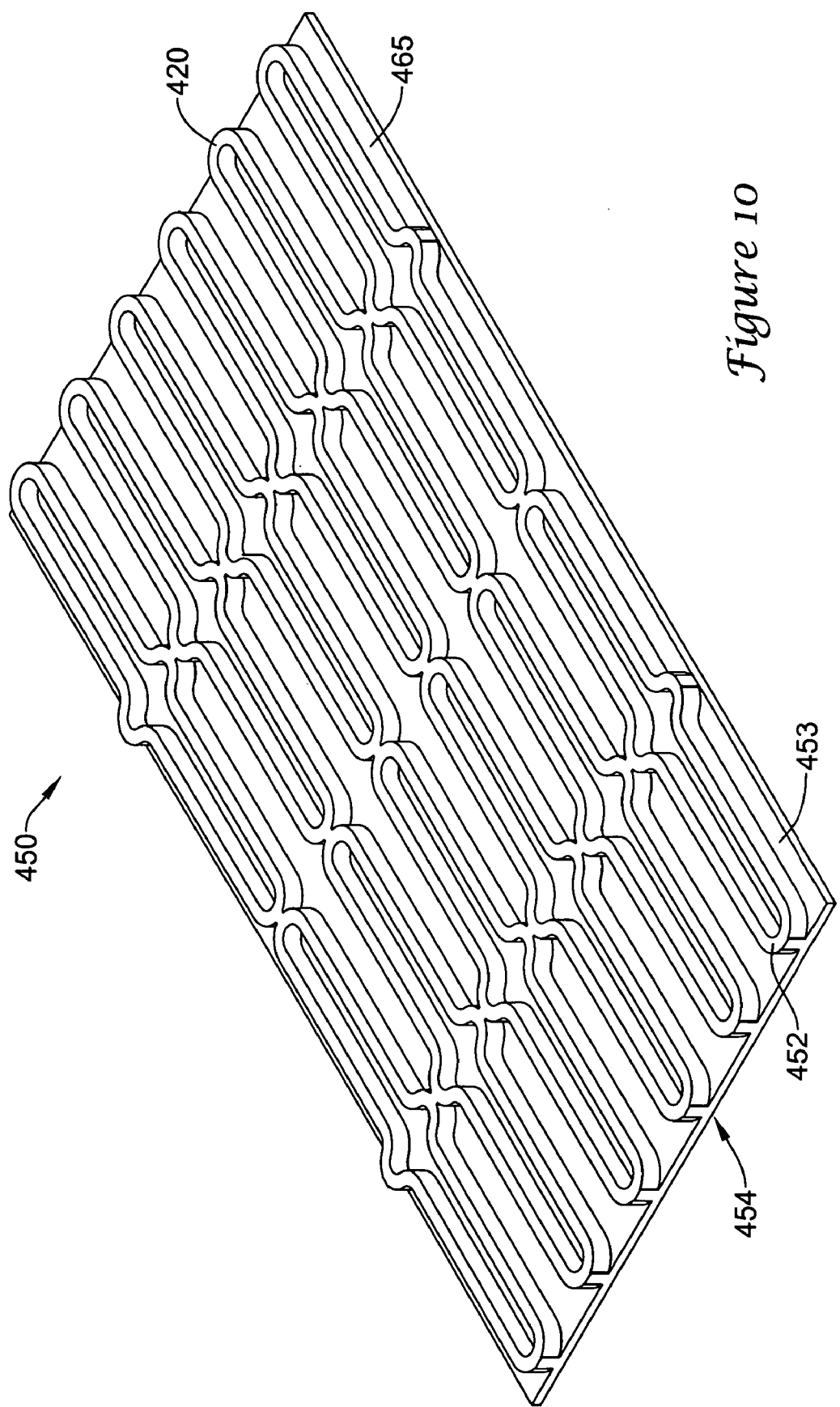
FIG. 10 is an enlarged perspective view of an alternative workpiece including a structural framework of a stent having a raised surface and a residuum layer of material having a recessed surface relative to the structural framework.

FIG. 10 is an enlarged view of an alternate embodiment of a structural framework 420 formed in a workpiece 450. A portion of the material of the workpiece 450 may be removed in order to demarcate the structural framework 420 of the stent 410 from a residuum layer of material 465 of the workpiece 450. Thus, the structural framework 420 may have a raised surface 452 relative to a recessed surface 453 of the residuum layer of material 465 remaining. The second surface 454 of the workpiece 450 may remain substantially intact. In some embodiments, the second surface 454 may be uninterrupted by cuts or breaks. Thus, the residuum material 465 may connect adjacent portions of the structural framework 420 such that the structural and/or dimensional integrity of the structural framework 420 is maintained. The residuum material 465 may be removed during a subsequent manufacturing process. For example, the residuum layer of material 465 may be removed during a chemical-etching or electro-polishing process, or the residuum material 465 may be mechanically cut or laser ablated, in order to remove the residuum material 465 from the structural framework 420. Other means of removing the residuum layer of material 465 may include dissolving, eroding, dissipating, melting, or otherwise eliminating the residuum material 465. Additional methods known in the art may be used to remove the residuum material 465 from the structural framework 420.

Figure 11:
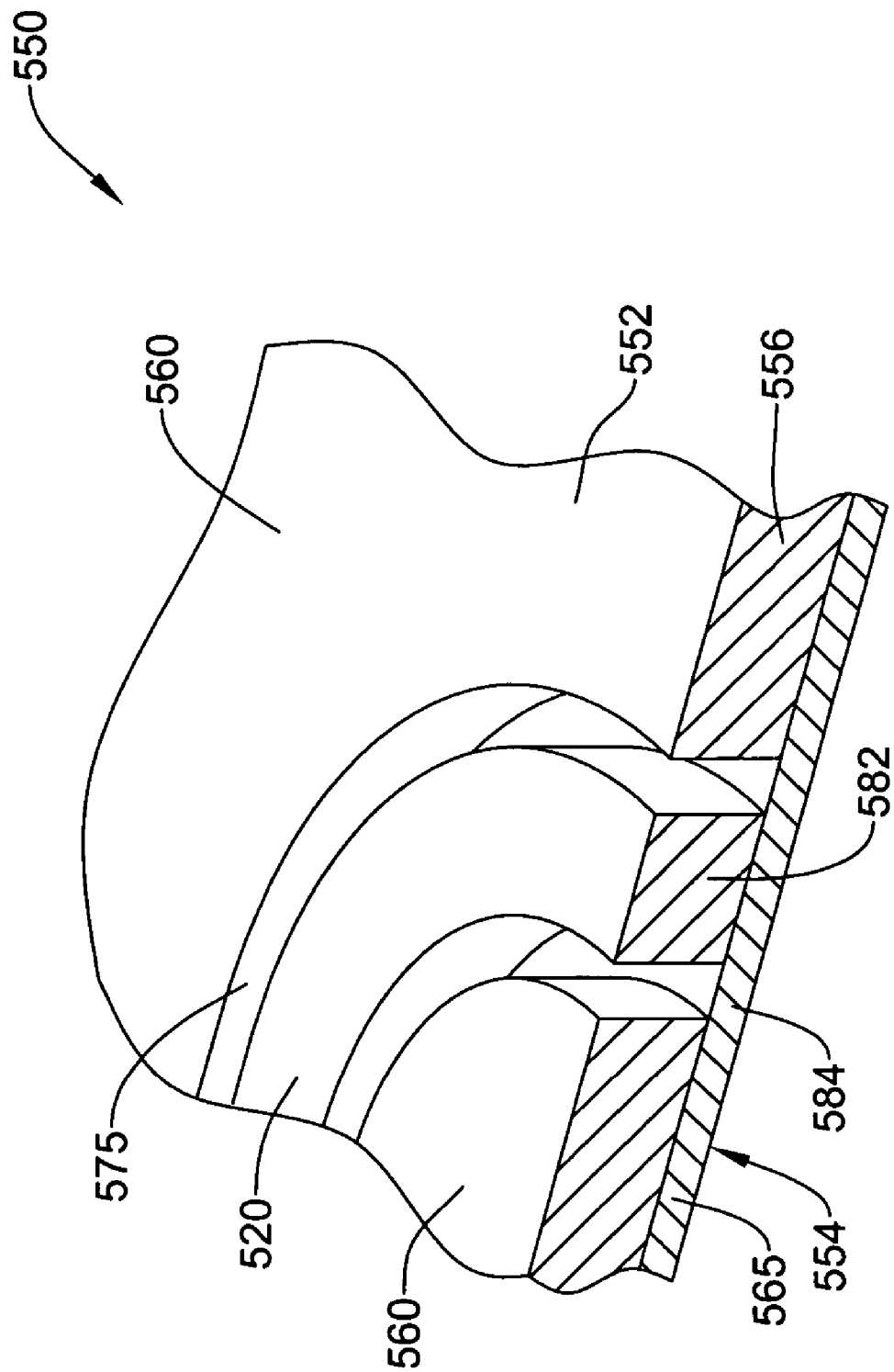
FIG. 11 is an enlarged perspective view of an alternative workpiece including a residuum layer of material which is dissimilar from the material of the structural framework.

FIG. 11 shows an enlarged view of an alternate embodiment of a structural framework 520 formed in a workpiece 550. Similar to previously discussed embodiments, a plurality of kerf channels 575 may be cut into the first surface 552 of the workpiece 550 to demarcate a structural framework 520 of a stent 510. The kerf channels 575 may extend only partially through the wall 556 of the workpiece 550. In this embodiment, the residuum layer of material 565 may be a layer of material dissimilar from the material comprising the remainder of the workpiece forming the structural framework 520 of the stent 510. For instance, the wall 556 of the workpiece 550 may be a laminated structure including a first layer of material 582 and a second layer of material 584 different from the first layer of material 582. The structural framework 520 may comprise the first layer of material 582 and the residuum layer of material 565 may comprise the second layer of material 584. One or more additional layers of material may be present in the wall 556. For example, a tie layer may be located between the first layer of material 582 and the second layer of material 584, affixing the first layer of material 582 to the second layer of material 584. In some embodiments, the second layer of material 584 may be a sleeve or liner extending through a tubular workpiece and partially defining an annular wall 556 of the workpiece 550. In some embodiments the first layer of material 582 may be secured to the second layer of material 584 by adhesive, bonding, welding, soldering, brazing, or the like.

The first layer of material 582 and the second layer of material 584 may be chosen for their individual, dissimilar laser energy absorbing properties. For instance, the material of the residuum layer 565 may not absorb laser energy or may absorb laser energy at a different level, frequency, wavelength, or degree than the material comprising the structural framework 520. For example, the first layer of material 582 may readily absorb laser energy at a first wavelength and the second layer of material 584 may readily absorb laser energy at a second wavelength different from the first wavelength. The first layer of material 582 may not readily absorb laser energy or may reflect laser energy at the second wavelength, or may absorb laser energy at the second wavelength to a lesser extent. The second layer of material 584 may not readily absorb laser energy or may reflect laser energy at the first wavelength, or may absorb laser energy at the first wavelength to a lesser extent. In some embodiments, the first wavelength may be in the near-infrared region, about 750 nm to about 2,500 nm, or the mid-infrared region, about 2,500 nm to about 10 µm, and the second wavelength may be in the far-infrared region, about 10 µm to about 1 mm. In other embodiments, the first wavelength may be in the far-infrared region and the second wavelength may be in the near-infrared region or the mid-infrared region. In some embodiments, the material of the structural framework 520 may absorb laser energy and the residuum layer of material 565 may reflect laser energy.

For example, the first layer of material 582 may comprise a metal, a metal alloy, or other metallic material, which may readily absorb laser energy emitted from a YAG laser. YAG lasers commonly emit laser energy having a relatively short wavelength in the near-infrared region or the mid-infrared region, which may be in the range of about 1000 nm to about 3000 nm. For instance, an Nd:YAG laser commonly emits energy in the near-infrared region having a wavelength of about 1064 nm or about 1320 nm. An Er:YAG laser commonly emits energy in the mid-infrared region having a wavelength of about 2940 nm. A YAG laser may be unsuitable for readily cutting a polymeric material or other material not compatible with the emitted wavelength of the laser.

The second layer of material may comprise a polymer or other material, which may readily absorb laser energy emitted from a $CO_2$ laser. $CO_2$ lasers commonly emit laser energy having a relatively long wavelength in the far-infrared region, such as in the range of about 9,300 nm to about 10,600 nm. Emitted energy from a $CO_2$ layer may tend to be reflected off of most metallic surfaces. Thus, a $CO_2$ laser may be unsuitable for readily cutting a metallic material or other material not compatible with the emitted wavelength of the laser. In some embodiments, the first layer of material 582 may comprise a polymeric material and the second layer of material 584 may comprise a metallic material.

Therefore, laser energy emitted from a laser may be absorbed by the first layer of material 582, but not be absorbed, be absorbed to a lesser extent, or be reflected by the second layer of material 584. For instance, laser energy of a YAG laser may cut through a metallic material, but not cut through a polymeric material, or laser energy of a $CO_2$ laser may cut through a polymeric material, but not cut through a metallic material.

Laser energy directed at the workpiece 550 may be readily absorbed by the first layer of material 582, thus cutting through the first layer of material 582. However, the laser energy may not be readily absorbed, be absorbed to a lesser extent, or may be reflected by the second layer of material 584. Thus, the second layer of material 584 may remain substantially uncut during the laser-cutting process. The second surface 554 of the workpiece 550 may be uninterrupted by cuts or breaks during the cutting process. As a result, the kerf channels 575 may be formed in the workpiece 550. As noted above, the kerf channels 575 may extend completely through the first layer of material 582, but may not extend through the second layer of material 584. Therefore, the structural framework 520 of the stent may be cut from the first layer of material 582, leaving a residuum layer of material 565 comprising the second layer of material 584 secured to the structural framework 520.

The residuum layer of material 565, not severed during the cutting process, may provide structural and/or dimensional integrity to the workpiece 550. Thus, the residuum layer of material 565 may provide support to the structural framework 520 during subsequent handling/processing of the stent. The residuum layer of material 565 may be removed from the structural framework 520 during a post-cutting process and prior to providing a finished stent. For example, the residuum layer of material 565 may be dissolved, dissipated, eroded, melted, mechanically separated, or otherwise removed from the structural framework 520. Thus, the waste material 560 may be completely separated from the structural framework 520 of the workpiece 550.

Figure 12:
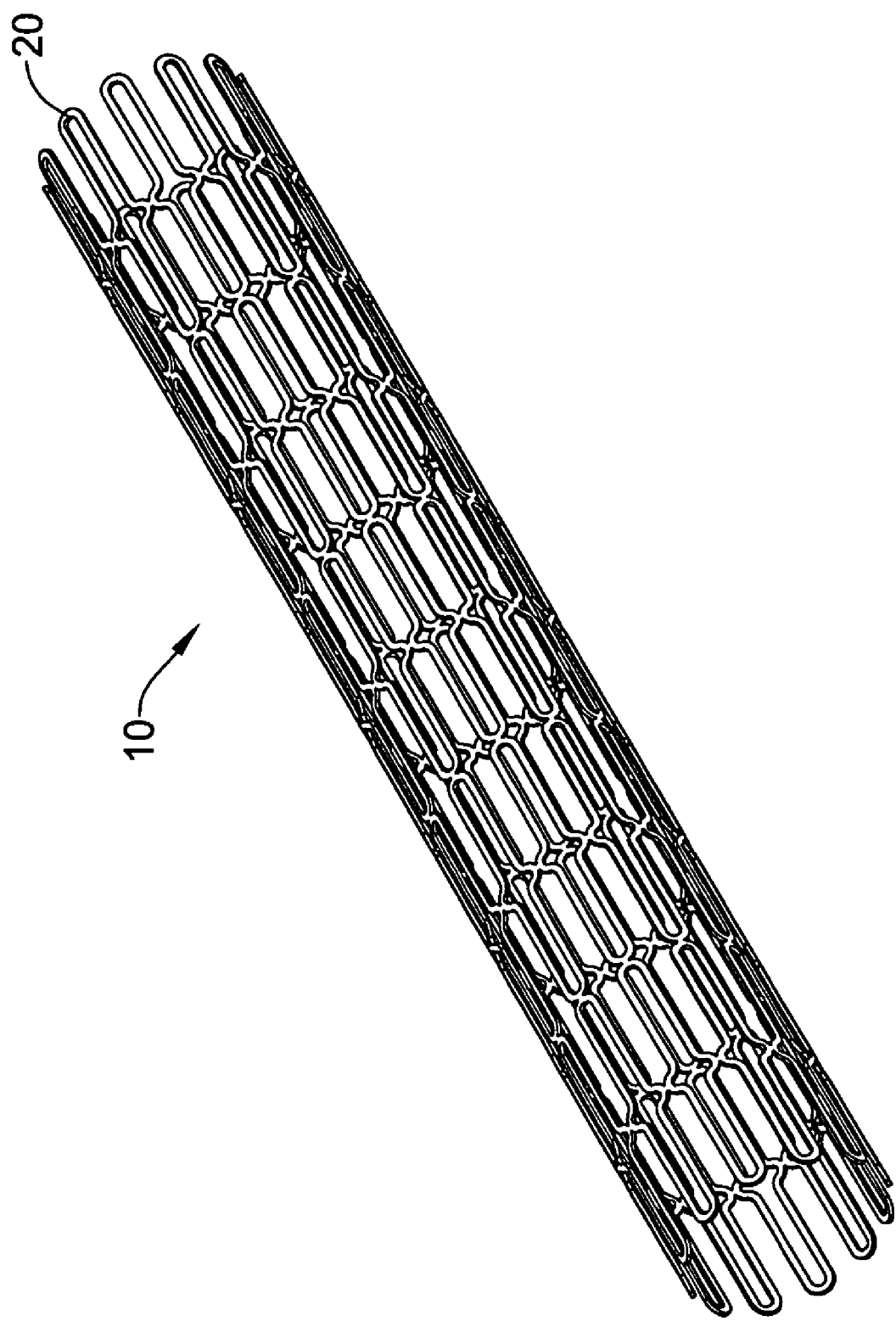
FIG. 12 is perspective view of a structural framework of a stent in accordance with the invention having waste material of the workpiece removed while in an unexpanded state.

FIG. 12 shows a stent 10 with the waste material 60 and the residuum material 65 removed. The waste material 60 (FIG. 7) and/or the residuum material 65 (FIG. 7) may be removed during one or more additional processes subsequent to cutting the kerf channels 75 in the workpiece 50 or otherwise removing material from the workpiece 50 to demarcate the structural framework 20 of the stent 10. The waste material 60 and/or the residuum material 65 may be removed by chemical-etching (otherwise known as chemical milling, photo-etching, or photo-chemical machining), electro-polishing, milling, punching, laser ablation, mechanical cutting, fracturing, or the like.

The structural and/or dimensional integrity of the structural framework 20 of the stent 10 may be maintained throughout the cutting process, as well as post-cutting processes performed on the workpiece. For instance, after the structural framework 20 is demarcated from the waste material of a workpiece comprising a flat sheet, the sheet may be formed into a tubular configuration. For example, the first edge 58 and second edge 59 of the workpiece 50 (as shown in FIG. 3) may be adjoined to form a tubular member. In some embodiments, the edges 58, 59 may be secured together. For example, the edges 58, 59 may be secured by an adhesive, welding, soldering, brazing, bonding, mechanically coupling, crimping, swaging, or the like. Because the residuum material remains attached to the structural framework while forming the framework into a tubular member, the integrity of the stent is enhanced.

The workpiece may be subjected to additional or alternative post-cutting processes prior to completely removing the waste material from the structural framework of the stent. For example, the workpiece may undergo a cleaning process, a heat treating process, a forming process, an annealing process, a thermal setting process, a strength hardening process, or similar process. Handling and/or manipulating the workpiece may be improved due at least in part to the structural and/or dimensional integrity afforded by the residuum layer of material connected to the structural framework of the stent.

Any one of the previously described stent forming processes may include one or more further processing steps. For example, the structural framework may be expanded or contracted. For instance, the structural framework may be placed over a mandrel in order to expand the structural framework. Additionally, or alternatively, the structural framework may be compressed into a reduced size, such as into a delivery configuration. Additionally, the structural framework of the stent may be subjected to a cleaning process to remove dross or residue subsequent to a cutting process. For instance, an alcohol and/or water solution may be used to clean foreign material from the workpiece. A chemical-etching process may be used to remove waste material and/or other material from the workpiece to provide a surface with no sharp edges or burrs. An electro-polishing process may be used to remove waste material and/or other material to reduce the surface roughness of the workpiece and provide a stent having a substantially smooth outer surface. An electro-polishing process, or similar electrical process, may also be used to dissolve, dissipate, erode or otherwise separate selected portions of material from the structural framework of the stent. For example, an electro-polishing process may dissolve a percentage of the mass of the material forming the stent. By dimensioning portions of the workpiece relatively small compared to the interconnected segments of the structural framework of the stent, the undesired portions of material will completely dissolve, dissipate, erode or otherwise be separated from the structural framework of the stent without fully dissolving the interconnected segments during an electro-polishing process. An electrical current of a sufficient magnitude may be applied to the workpiece to separate the waste material from the structural framework of the stent. Additionally, a stent may be subjected to one or more heat treating processes in order to remove residual stresses and/or provide favorable characteristics to the stent, such as shape memory properties.

It is noted that although the disclosed processes and methods have been discussed regarding the formation of a stent, such processes and methods may also be utilized to form other stent configurations, as well as other medical devices such as guidewires, coil tips, balloon delivery components, filter mesh, filter devices, retrieval devices, and other medical devices.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A method of manufacturing a stent, comprising:
   providing a workpiece including a wall having a thickness defined between a first surface and a second surface;
   cutting a plurality of kerf channels in the first surface of the workpiece, wherein each kerf channel includes a first edge, a second edge and a bottom surface extending between the first and second edges such that the kerf channels extend only partially through the wall of the workpiece, and wherein the plurality of kerf channels demarcate a structural framework of the stent from a waste material connected to the structural framework by a residuum material of the workpiece located between the bottom surface of the kerf channels and the second edge of the workpiece; and
   subsequently removing the residuum material and the waste material from the structural framework.

2. The method of claim 1, wherein the step of removing the residuum material includes electropolishing the workpiece.

3. The method of claim 1, wherein the step of removing the residuum material includes chemical-etching the workpiece.

4. The method of claim 1, further comprising the step of expanding the structural framework.

5. The method of claim 4, wherein the step of expanding the structural framework is performed after the step of removing the residuum material and the waste material from the structural framework.

6. A method of manufacturing a stent, comprising:
   providing a workpiece including a wall having a thickness defined between a first surface and a second surface;
   laser cutting a plurality of kerf channels in the first surface of the workpiece, wherein each kerf channel includes a first edge, a second edge and a bottom surface extending between the first and second edges;
   wherein the plurality of kerf channels demarcate a structural framework of the stent from waste material of the workpiece such that the first surface of the workpiece has a raised portion defining the structural framework and a recessed portion defining a residuum layer of material connecting the waste material with the structural framework;
   subsequently removing the waste material from the structural framework; and
   expanding the structural framework after removing the waste material from the structural framework.

7. The method of claim 6, wherein the plurality of kerf channels outline the structural framework.

8. The method of claim 6, wherein the plurality of kerf channels form a plurality of closed pathways.

9. The method of claim 6, wherein the step of removing the waste material includes dissipating the residuum layer of material during a chemical-etching process.

10. The method of claim 6, wherein the step of removing the waste material includes dissipating the residuum layer of material during an electropolishing process.

11. The method of claim 6, further comprising the step of electropolishing the workpiece.

12. The method of claim 6, further comprising the step of rolling the workpiece into a tubular stent.

13. The method of claim 6, further comprising the step of heat treating the workpiece.

* * * * *

UNITED STATES PATENT AND TRADEMARK OFFICE
CERTIFICATE OF CORRECTION

| | |
|---|---|
| PATENT NO. | : 7,647,687 B2 |
| APPLICATION NO. | : 11/226633 |
| DATED | : January 19, 2010 |
| INVENTOR(S) | : Koch et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1162 days.

Signed and Sealed this

Sixteenth Day of November, 2010

David J. Kappos
*Director of the United States Patent and Trademark Office*